(12) United States Patent
    Alhourani (10) Patent No.: US 10,335,030 B2
(45) Date of Patent: Jul. 2, 2019

(54) RAKAN'S ADJUSTABLE GLAUCOMA VALVE AND SHUNT WITH INTRAOCULAR PRESSURE INDICATOR AND RASHA'S POSTERIOR—ANTERIOR CHAMBER SHUNT

(71) Applicant: Rakan Elias Jamil Alhourani, Alfuhais (JO)

(72) Inventor: Rakan Elias Jamil Alhourani, Alfuhais (JO)

( * ) Notice: Subject to any disclaimer, the term of this patent is extended or adjusted under 35 U.S.C. 154(b) by 298 days.

(21) Appl. No.: 15/464,352

(22) Filed: Mar. 21, 2017

(65) Prior Publication Data
    US 2018/0271700 A1    Sep. 27, 2018

(51) Int. Cl.
    *A61B 3/16*    (2006.01)
    *A61F 9/007*   (2006.01)

(52) U.S. Cl.
    CPC ............. *A61B 3/16* (2013.01); *A61F 9/00781* (2013.01); *A61F 2230/0069* (2013.01); *A61F 2250/0013* (2013.01); *A61F 2250/0069* (2013.01); *A61F 2250/0091* (2013.01)

(58) Field of Classification Search
    CPC ............... A61B 3/16; A61F 2230/0069; A61F 2250/0013; A61F 2250/0091; A61F 9/00781; A61F 9/0017
    See application file for complete search history.

*Primary Examiner* — Leslie R Deak (57) ABSTRACT

The present invention is a device that is used for glaucoma management by using an adjustable shunt that drains the aqueous humour from inside the eye in a precise way. This new device has a valve that prevents back flow of the drained fluid and that decreases the risk of hypotony, and also this device has an intraocular pressure indicator. In addition to the main device, there is a small device that is implanted throughout the iris, in order to shunt aqueous humour from posterior chamber to anterior chamber of the eye.

1 Claim, 15 Drawing Sheets

RAKAN'S ADJUSTABLE GLAUCOMA VALVE AND SHUNT WITH INTRAOCULAR PRESSURE INDICATOR AND RASHA'S POSTERIOR—ANTERIOR CHAMBER SHUNT

CROSS-REFERENCES TO RELATED APPLICATIONS

Not Applicable

STATEMENT REGARDING FEDERALLY SPONSORED RESEARCH OR DEVELOPMENT

Not Applicable

NAME OF THE INVENTOR

Rakan Elias Jamil Alhourani

STATEMENT REGARDING PRIOR DISCLOSURES BY THE INVENTOR OR A JOINT INVENTOR

Not Applicable

FIELD OF THE INVENTION

The present invention generally relates to a device that shunts aqueous humour from inside the eye/anterior chamber to outside the eye/sub tenon's space. In this device, the amount and rate of fluid shunted is adjustable and it has a valve and an intraocular pressure indicator (IOP). In addition to the main device, there is a small device to shunt aqueous humour from posterior chamber to anterior chamber of the eye.

BACKGROUND OF THE INVENTION

Rakan's adjustable glaucoma valve and shunt with an IOP indicator has an application in managing many glaucoma types, this new device can adjust the IOP in a precise way with a valve that prevents back flow of the shunted aqueous humour and it prevents unwanted "decrease in IOP"/"hypotony", by blocking drainage when the IOP is abnormally low. And this new device has an indicator that helps the patient to know the IOP status or even to know the exact measurement of the IOP with just checking the indicator, which helps manage any early increase in the IOP by seeking doctor's help immediately.

So Rakan's adjustable glaucoma valve and shunt with an IOP indicator will allow us to control IOP accurately with the ability to readjust the flow rate/IOP and prevents hypotony, and will allow the patient to self monitor his/her IOP.

Rasha's posterior—anterior chamber shunt is a new small device that shunts aqueous humour from the posterior chamber to the anterior chamber of the eye, by using a small tube with a special design that stabilizes the device and that prevents the light to pass through it.

SUMMARY OF THE INVENTION

The present invention is a device that manages glaucoma by draining aqueous humour using an adjustable shunt to precisely control IOP. This new device also has a valve that prevents back flow of the drained fluid and that decreases the risk of hypotony, in addition to that this device has an intraocular pressure indicator.

In addition to the main device, there is a small device that is implanted through the iris, to shunt aqueous humour from posterior chamber to anterior chamber of the eye.

DETAILED DESCRIPTION OF THE INVENTION

Figure 1:
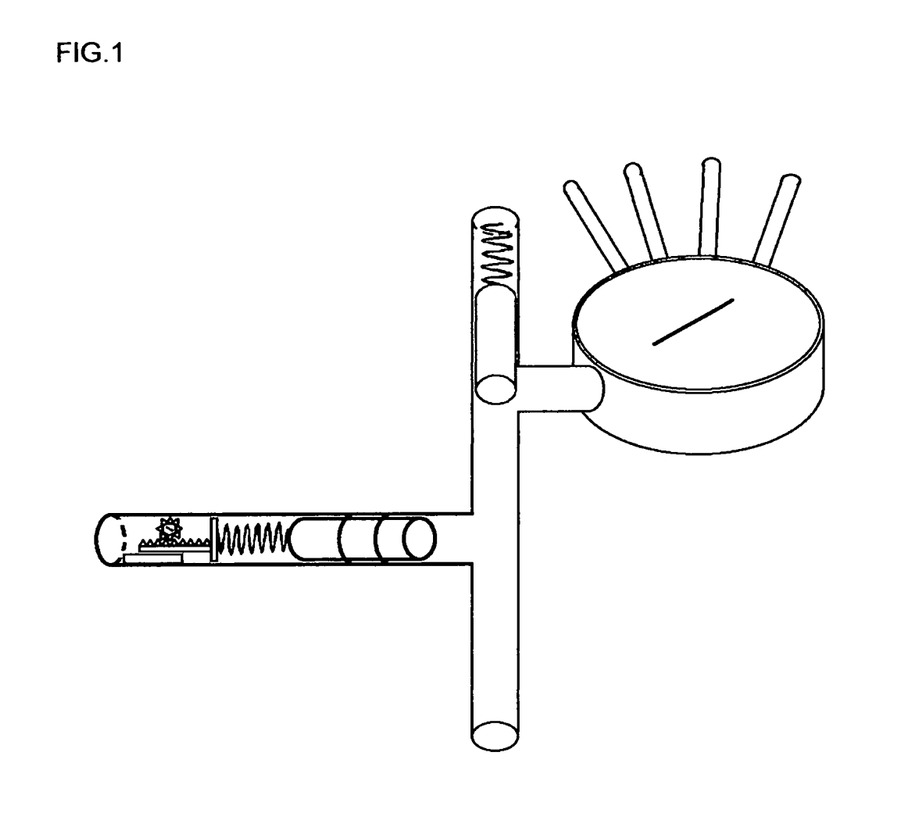
FIG. 1: General view of Rakan's adjustable glaucoma valve and shunt with intraocular pressure indicator.
Figure 2:
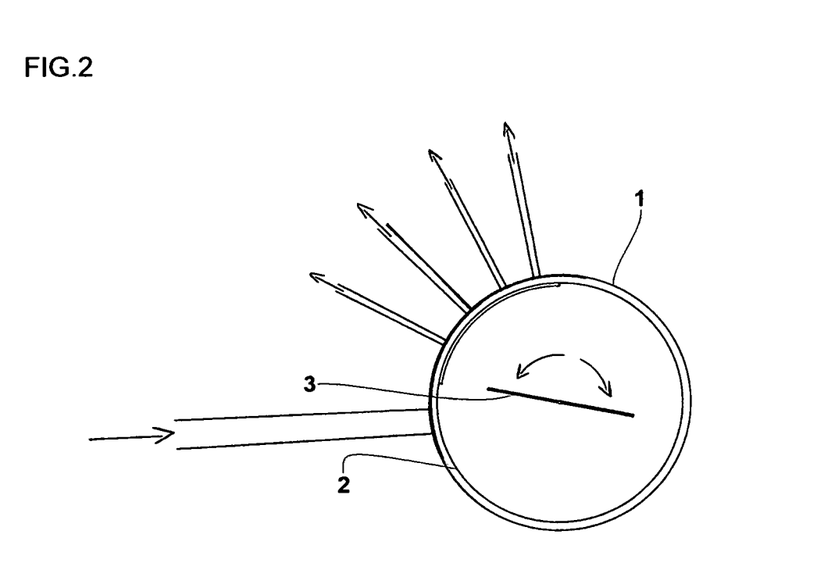
FIG. 2: The cylindrical adjustable shunt with one inlet tube and four outlet tubes, the straight arrows illustrate the direction of fluid movement, and the curved arrows illustrate the rotatory directions.
Figure 3:
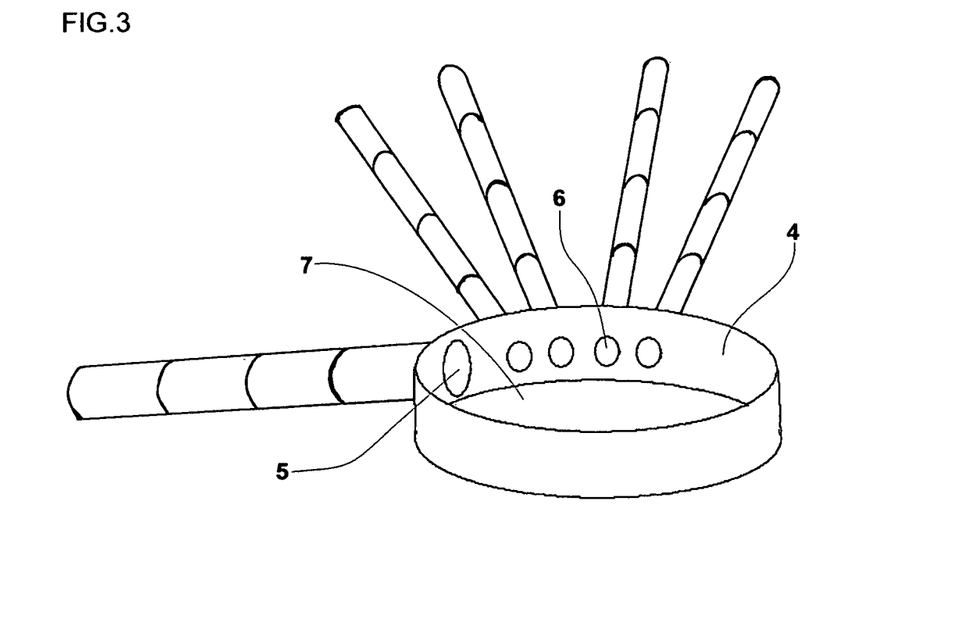
FIG. 3: The outer cylindrical piece of the cylindrical adjustable shunt with one inlet tube and four outlet tubes.

Rakan's adjustable glaucoma valve and shunt with intraocular pressure indicator FIG. 1 consists of three parts: shunt, valve and indicator, and it uses the same material used in the ordinary glaucoma shunts or valves. The first part FIG. 2: the adjustable shunt comprises two pieces; The outer piece 1/FIG. 3 is cylindrical in shape, fixed not movable, its side wall 4 (curved surface) is entirely covered except for multiple openings that connect the shunt with one or more bigger tubules (inlet openings 5) and with multiple smaller tubules (outlet openings 6), the flat base surface 7 is covered and the top of the outer cylindrical piece is uncovered (open).

Figure 4:
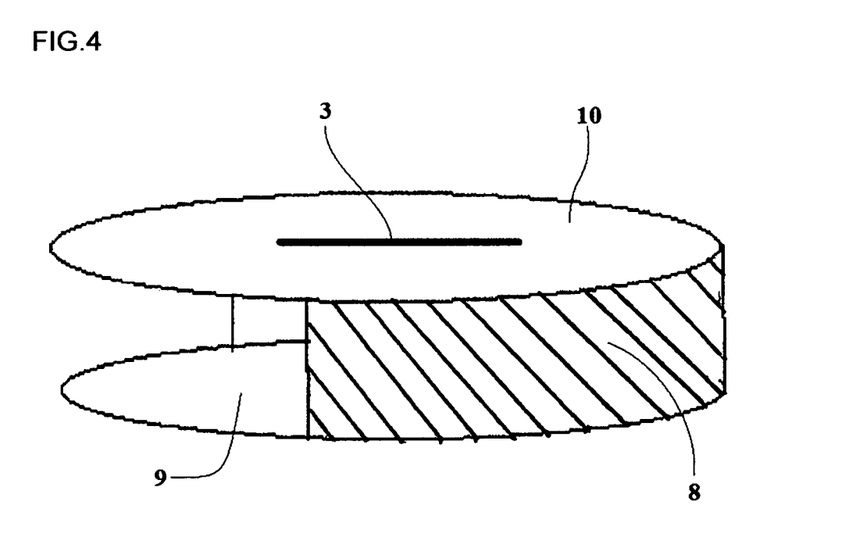
FIG. 4: The inner cylindrical piece of the cylindrical adjustable shunt with the covered area situated toward the front.
Figure 5:
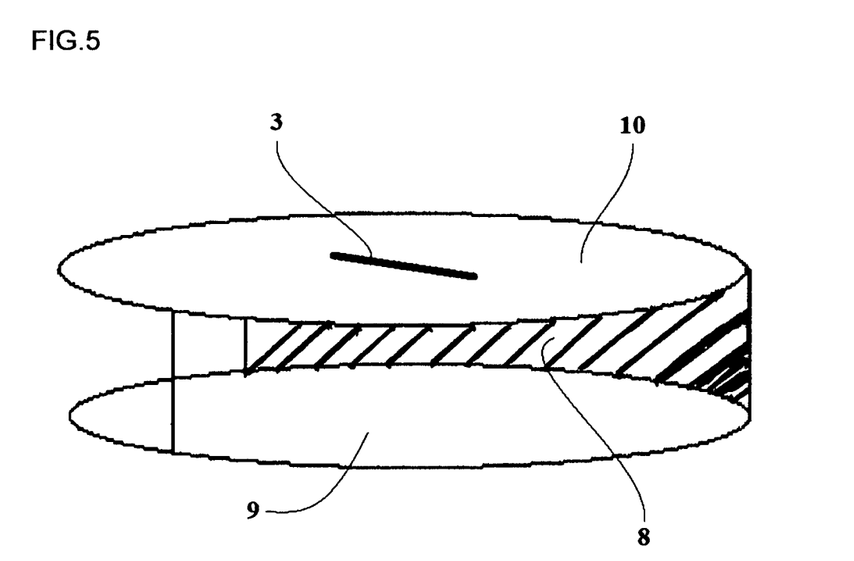
FIG. 5: The inner cylindrical piece of the cylindrical adjustable shunt with the covered area situated toward the back.
Figure 6:
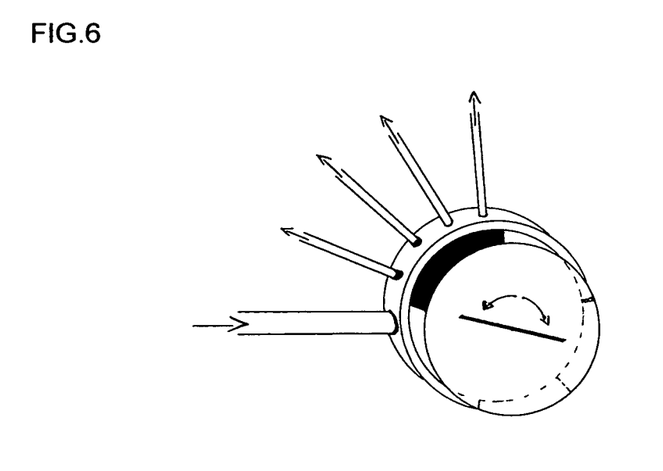
FIG. 6: The cylindrical adjustable shunt (the inner piece is elevated for illustration)—the covered area is situated against the outlet openings. Straight arrows show the direction of fluid movement, and curved arrows show the rotatory directions.
Figure 7:
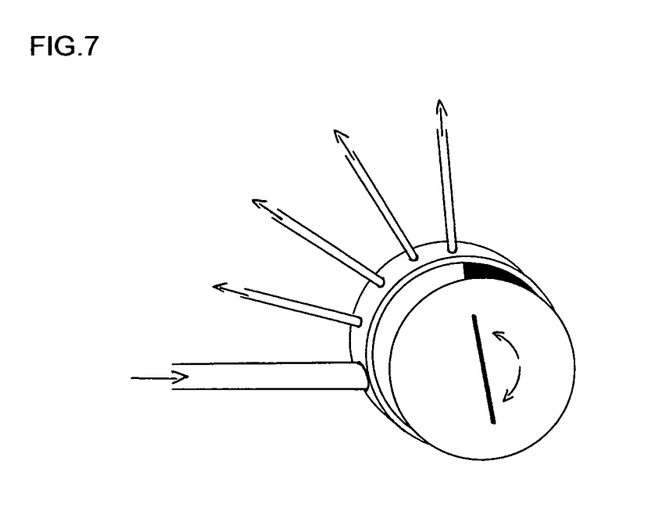
FIG. 7: The cylindrical adjustable shunt (the inner piece is elevated for illustration)—the covered area is situated away from the outlet openings. Straight arrows show the direction of fluid movement, and curved arrows show the rotatory directions.
Figure 8:
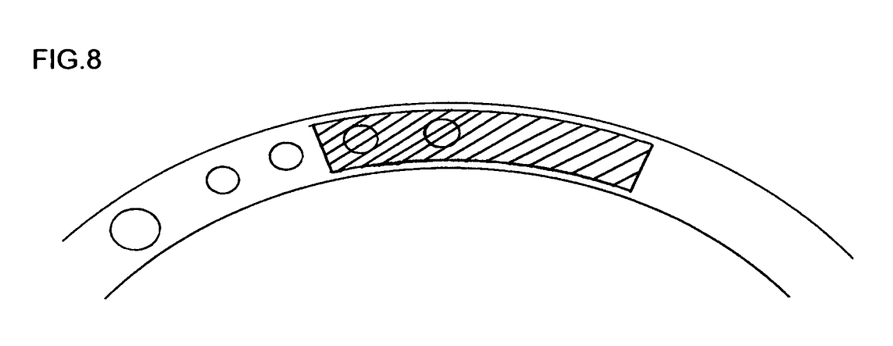
FIG. 8: Illustration view for the relation between the curved covered area and the outlet openings.

The inner piece of the adjustable shunt 2/FIG. 4/FIG. 5 is cylindrical in shape and fits/settles inside the outer piece, it is rotatory not fixed, its flat circular base 9 is covered, its curved side 8 surface is partially covered with almost one third to one half of the area covered only, this covered area obstructs and closes the outlet openings of the outer piece when is placed against them FIG. 6 and when the covered area is rotated away, the outlets are opened FIG. 7, so we can control how many openings are closed or opened, by rotating the covered part of the inner cylindrical piece curved side surface FIG. 8, and this eventually will control the drainage rate of the shunt which after all determines the intraocular pressure (IOP), the circular flat top 10 of the inner piece is covered and contains a handle 3 by which we can rotate the whole structure of the inner cylindrical piece of the shunt so we can control the location of the covered area of the curved side surface FIG. 4/FIG. 5 which will determine the number of closed and opened outlet openings.

Figure 9:
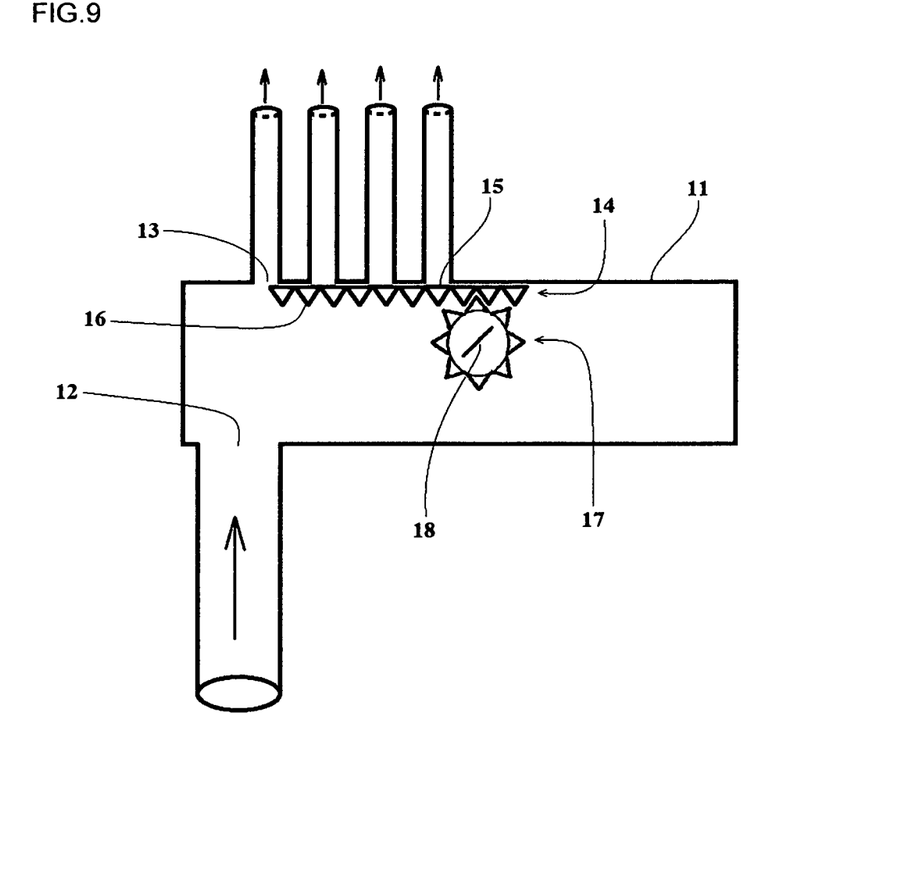
FIG. 9: An adjustable shunt using a straight cover slide. Straight arrows show the direction of fluid movement.

In addition to the cylindrical shaped designs, other designs can be used for Rakan's adjustable shunt, such as using a straight cover slide FIG. 9 rather than a curved one. This design generally comprises three pieces: first piece—the container 11, is fixed (not movable), its base is covered, its side walls are covered except for the outlet 13 and inlet 12 openings and its top has an opening for the top surface of the rotatory toothed adjustable small cylinder 17.

Figure 10:
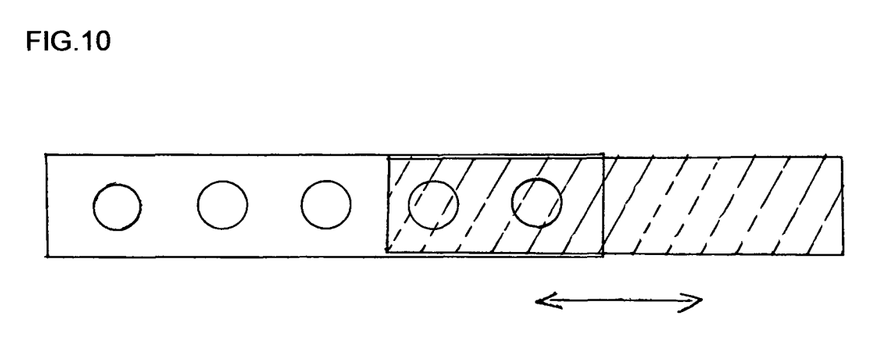
FIG. 10: Illustration view for the relation between the straight cover slide and the outlet openings. The arrow shows the direction of movement.

Second piece—the sliding cover 14, it is movable so it can cover or uncover the outlet openings FIG. 10, it has a flat surface 15 which faces the outlet openings and a toothed surface 16 which engages with the rotatory toothed adjustable small cylinder 17. Third piece—the rotatory toothed adjustable small cylinder 17, it is rotatory, its curved side surface which is toothed engages with and moves the second piece, and its circular top surface contains a handle 18 by which we can rotate the whole cylinder.

Figure 11:
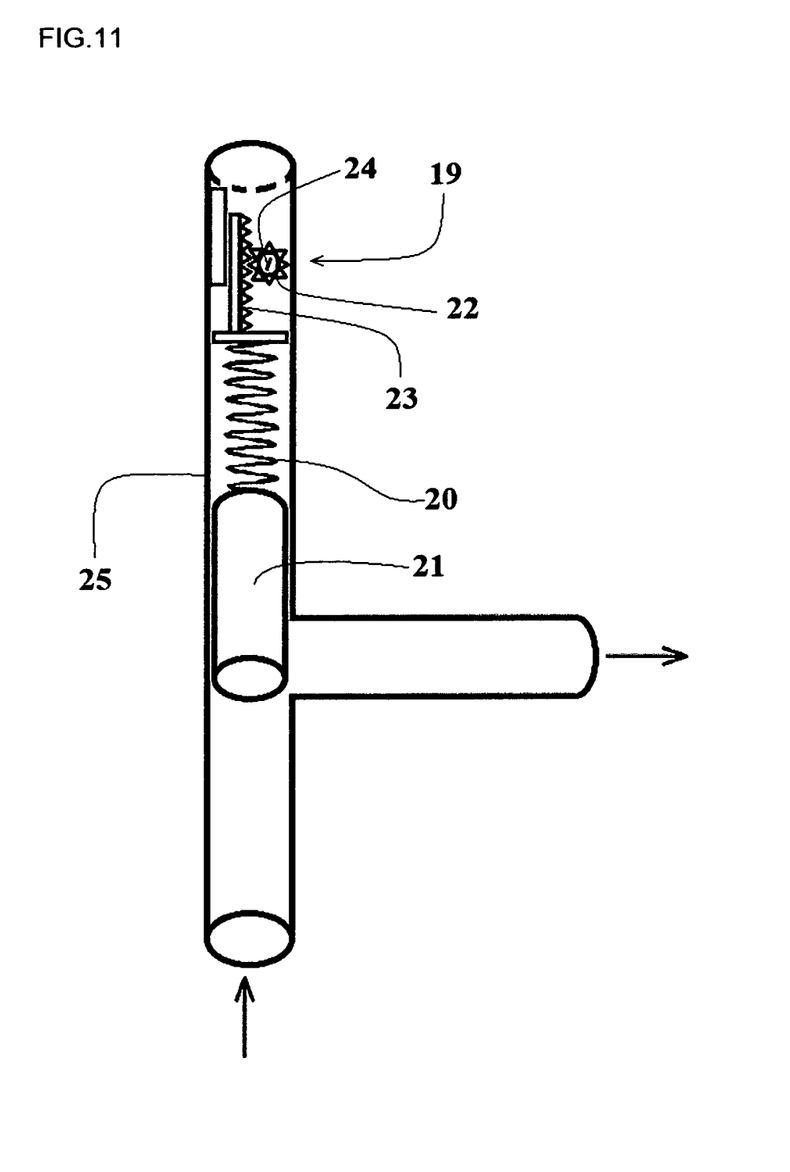
FIG. 11: Rakan's adjustable spring valve. Straight arrows show the direction of fluid movement.
Figure 12:
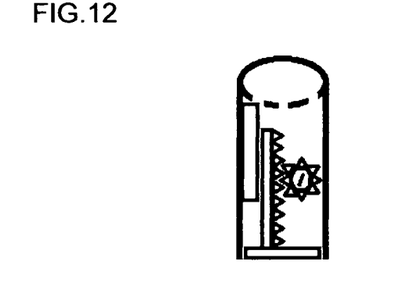
FIG. 12: The first part of Rakan's adjustable spring valve—the adjustable structure.

The second part: the adjustable spring valve FIG. 11 comprises three parts; the first part—the adjustable structure 19/FIG. 12: contains a rotatory toothed adjustable small cylinder 22 that is engaged with a toothed shaft 23, this shaft is connected to the second part (the spring 20) and it moves forward and backward according to the direction of the cylinder rotation, the rotatory cylinder has a handle 24 on its circular flat top surface that can be rotated and adjusted. The second part—the spring 20: its compressing or squeezing amount is proportional to the IOP. The third part—the movable seal 21: the seal is placed between the inlet tube that receives aqueous humour from the eye and the outlet tube. The three parts are configured to be located in the valve container 25 which has an outlet and inlet tubes and has a circular opening for the handle of the rotatory toothed adjustable small cylinder of the adjustable structure.

When the pressure in the inlet tube is high enough it will push the seal away squeezing the spring, and as the seal is moved the outlet opening is unsealed or uncovered by the seal partially or completely, so the fluid can pass through the valve to the outlet tube and the aqueous humour will be drained out of the eye which will decrease the IOP, the adjustable structure will adjust the position of the spring and the seal, so it will determine the pressure needed to move the seal away from the outlet opening, the more the pressure the more the seal movement (displacement) and eventually more area of the outlet opens and more drainage. When the pressure is low the spring will push the seal back and close the outlet opening which prevents back flow and prevents excess drainage associated with hypotony.

Figure 13:
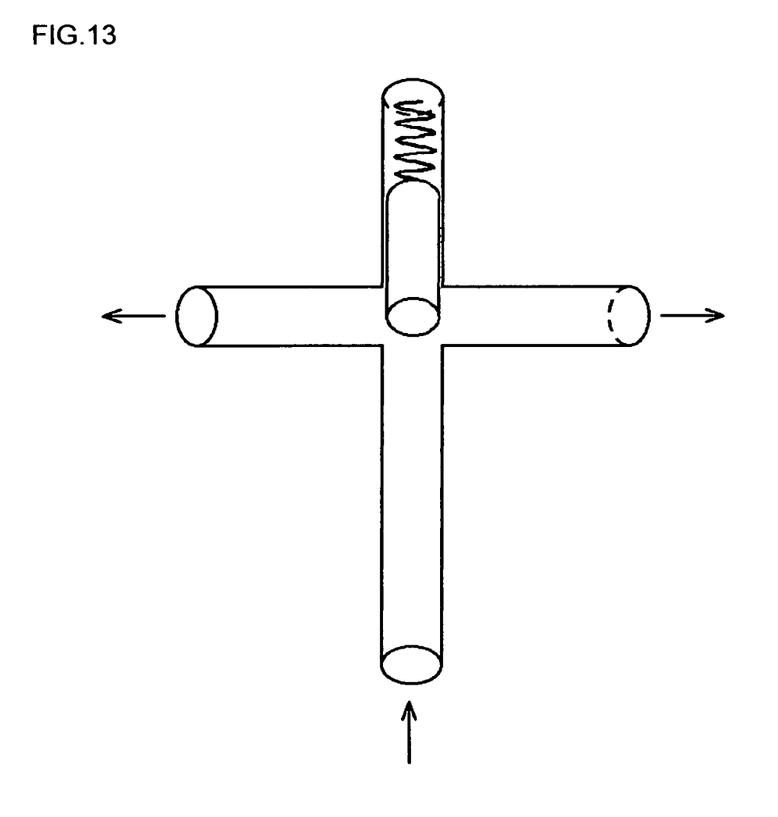
FIG. 13: Rakan's spring valve with two outlets in different directions. Straight arrows show the direction of fluid movement.
Figure 14:
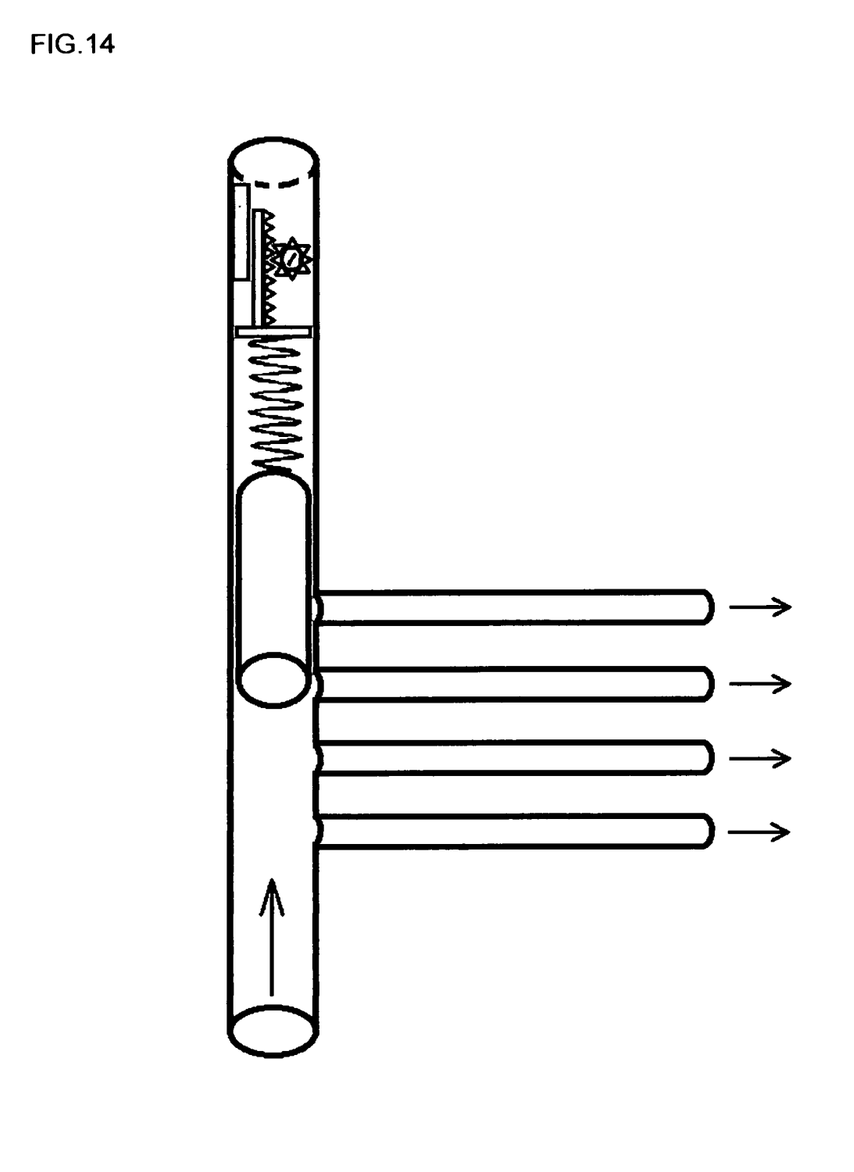
FIG. 14: Rakan's adjustable spring valve with multiple smaller outlets. Straight arrows show the direction of fluid movement.
Figure 15:
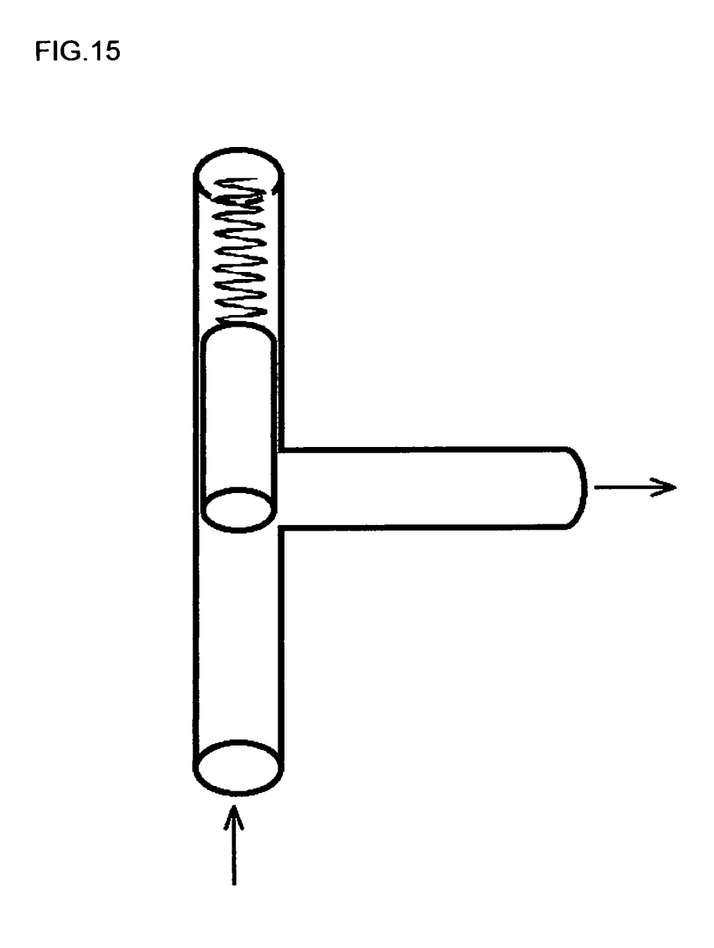
FIG. 15: Rakan's spring valve without an adjustable structure. Straight arrows show the direction of fluid movement.

The valve may have one or more outlet openings FIG. 13 or may have multiple smaller outlets FIG. 14 which will help in more control of drainage; as the seal is displaced more and more caused by a high inlet aqueous pressure, more outlets openings will be uncovered and more drainage occurs. Also the valve may not have the adjustable structure FIG. 15.

Figure 16:
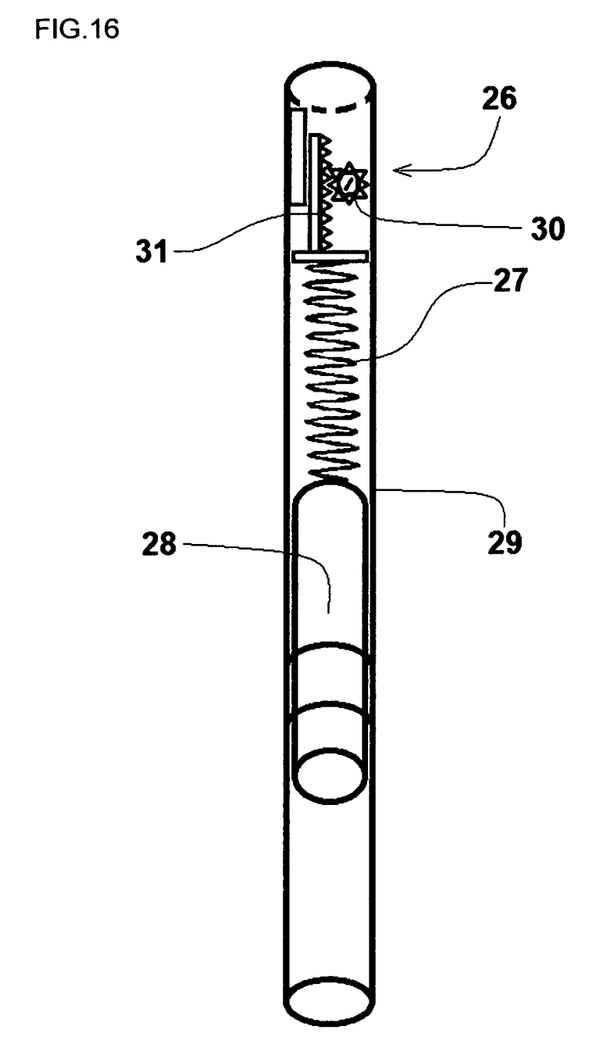
FIG. 16: Rakan's intraocular pressure indicator.
Figure 17:
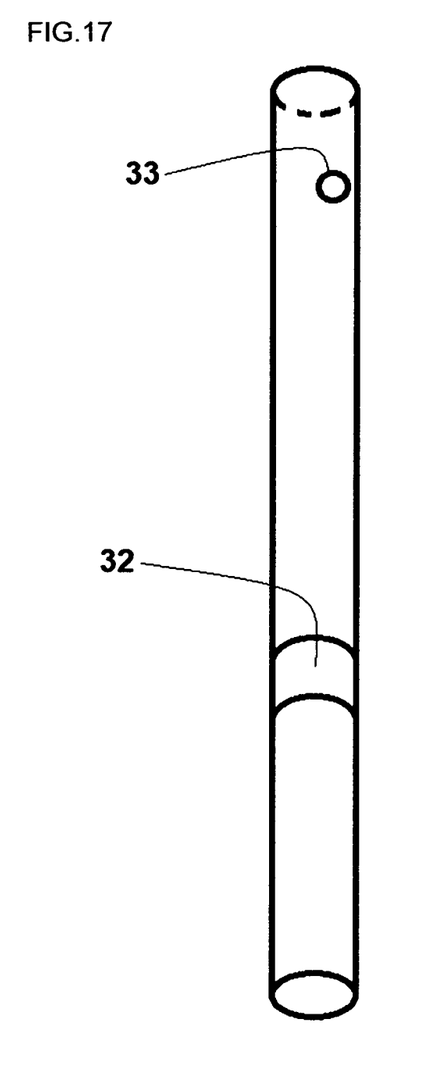
FIG. 17: The fourth part of Rakan's intraocular pressure indicator—the container: showing the transparent window and the adjustable cylinder top opening.

The third part: the intraocular pressure indicator FIG. 16 comprises four parts; the first part—the adjustable structure 26: contains a rotatory toothed adjustable small cylinder 30 that is engaged with a toothed shaft 31, this shaft is connected to the second part (the spring 27) and it moves forward and backward according to the direction of the cylinder rotation, the rotatory cylinder has a handle on its circular flat top surface that can be rotated and adjusted, its function is to recalibrate the indicator. The second part—the spring 27 its compressing or squeezing amount is proportional to the IOP. The third part—the movable seal 28: the amount of the seal displacement is proportional to the amount of pressure in the indicator connecting tube which connects the indicator to the inside of the eye, the seal has a range of different colors that can be checked through the transparent window 32 of the fourth part (the container 29) and each color indicates a pressure measurement, so when the pressure is too high the seal will be displaced further away toward the spring and the color appears through the indicator's window is dark red for an example, and when the pressure is too low the spring will push the seal further away in the other direction and the color appears through the indicator's window is light blue for an example, in addition to the colors, the seal can be marked with a range of numbers which imply the pressure measurement, the fourth part—the container 29/FIG. 17: it contains the other three parts and has a transparent window 32 through which we can see the color or the number indicated on the movable seal, and the container part has an opening 33 for the circular flat top surface of the cylinder.

Figure 18:
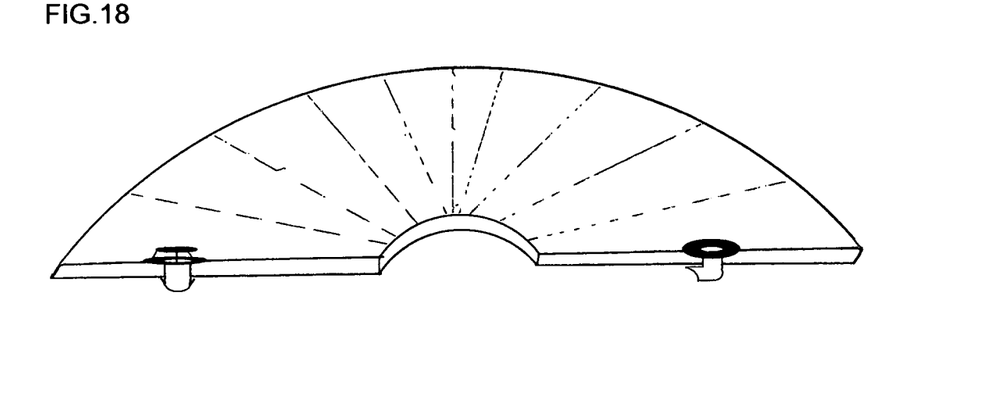
FIG. 18: Illustration view showing the iris cut with both designs for Rasha's posterior—anterior chamber shunt implanted.

Rasha's posterior—anterior chamber shunt FIG. 18 is a trans iris small tubule designed in a way that prevents any light rays to pass through, the color of the shunt is preferred to be dark or same as the iris color, and the shunt can be placed in already existing peripheral iridotomy or iridectomy or in any needed place.

Figure 19:
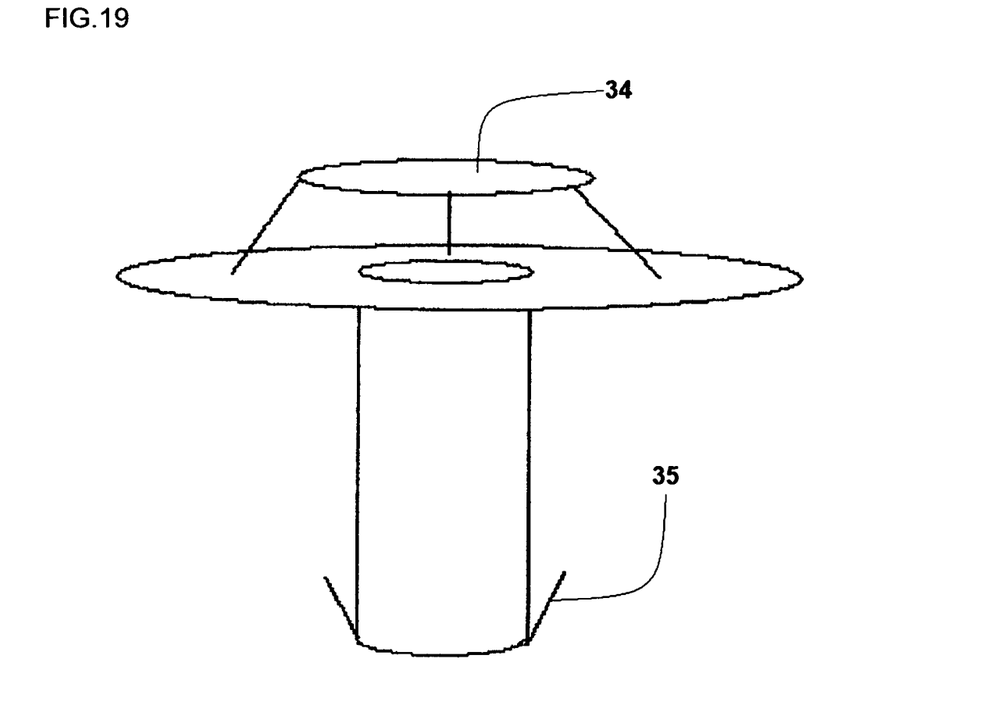
FIG. 19: Rasha's posterior—anterior chamber shunt—straight tubule design with a cap.
Figure 20:
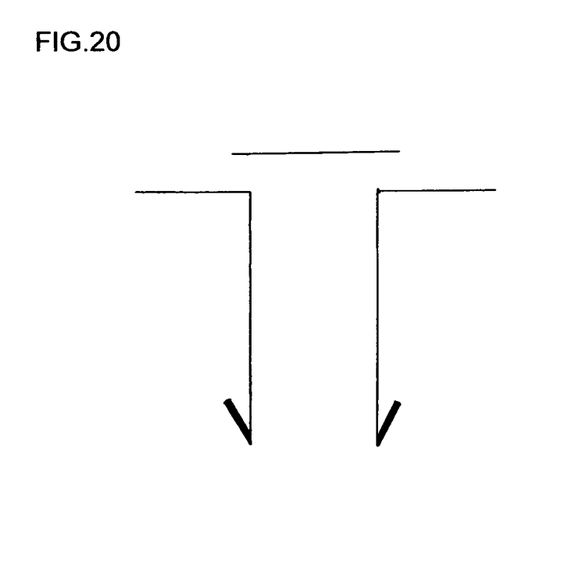
FIG. 20: A side slice/cut of Rasha's posterior—anterior chamber shunt—straight tubule design.
Figure 21:
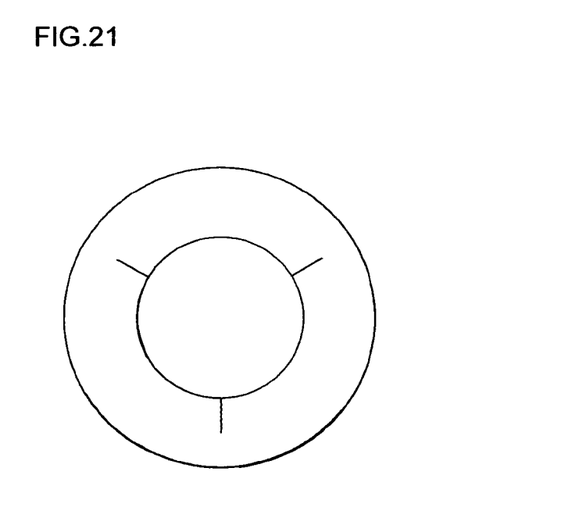
FIG. 21: Top view of Rasha's posterior—anterior chamber shunt—straight tubule design.
Figure 22:
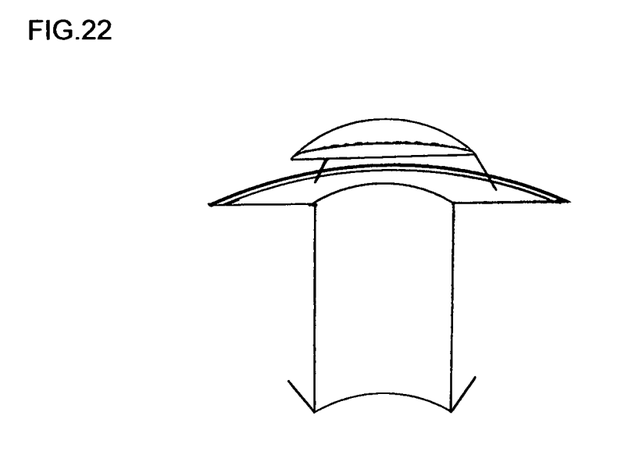
FIG. 22: Side view with side cut and intact cap of Rasha's posterior—anterior chamber shunt—straight tubule design.
Figure 23:
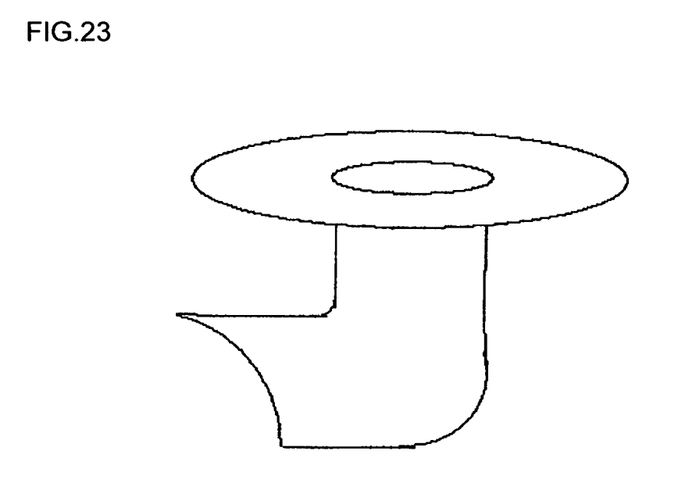
FIG. 23: Rasha's posterior—anterior chamber shunt—curved tubule design.

It could be a straight tubule design FIG. 19/FIG. 20/FIG. 21/FIG. 22, with a cap 34 covering its anterior chamber end and with a male buckle member structure 35 at its posterior chamber end, to prevent shunt displacement. And it could be a curved tubule design FIG. 23.

The invention claimed is:

1. An intraocular fluid drainage device comprises three parts: a first adjustable shunt part comprising an outer fixed piece and an inner rotatory piece:

said outer fixed piece is a hollow cylindrical-shaped container configured to receive the inner rotatory piece: said outer fixed piece comprises a side wall having multiple apertures;

wherein one aperture is configured as an inlet and the other apertures configured as outlets;

said outer fixed piece comprises a covered flat base circular surface and an open top surface; said inner rotatory piece is a hollow cylinder having a covered circular flat base surface, a covered circular top surface and a partial covered curved side surface; said circular top surface of the inner rotatory piece having a handle; said partial covered curved side surface of the inner piece configured to seal the outlets apertures of the outer fixed piece;

wherein the number of sealed outlets is controlled by rotating of the handle of the inner rotatory piece which rotates the partial covered curved side surface of the inner piece hence determining the number of the outlet apertures sealed of the outer fixed piece;

wherein controlling the number of the outlet apertures sealed controls the amount of drained out of the adjustable shunt part;

A second valve part comprising a spring and a movable seal; said spring and movable seal configured to fit in a tubular container; said tubular container comprises two tubules; an inlet tubule and an outlet tubule; said inlet tubule having one end covered and other end open; said inlet tubule having a side aperture configured to connect the outlet tubule; wherein the inlet tubule open end is configured to be placed in the anterior chamber of an eye; said spring is located between the covered end of the inlet tubule and the movable seal; said movable seal configured to seal the side aperture; said outlet tubule having two open ends; said outlet tubule is connected to the inlet tubule side aperture at one end and to the first adjustable shunt part at other end;

wherein fluid enters the inlet tubule pushes the movable seal and squeezes the spring hence opens the side aperture; wherein if fluid pressure is low in the inlet tubule the spring stretches and pushes the movable seal to seal the side aperture hence preventing backflow of fluid;

A third intraocular pressure indicator part comprising an adjustable structure, a spring; a sea, and a container, said adjustable structure having a rotatory toothed adjustable small cylinder and a toothed shaft: said rotatory toothed adjustable small cylinder having a handle: said rotatory toothed adjustable small cylinder configured to a get engaged with the toothed shaft;

Wherein rotating the handle rotates the toothed cylinder hence displacing the toothed shaft; said toothed shaft is connected to the spring of the indicator; said spring connects the adjustable structure to the sea of the indicator; said seal having a scale of colors; said container is a tubular structure having an opening for the handle of the rotatory toothed adjustable small cylinder of the adjustable structure; said container having a transparent window through which a color of the scale-colored seal appears: said container is connected to the inlet tubule of the valve part;

wherein the spring squeezing amount is proportional to fluid pressure facing the sea of the indicator hence the amount of displacement of the scale-colored seal hence the color appearing in the transparent window.

* * * * *